United States Patent
Glinec et al.

(10) Patent No.: US 9,838,670 B2
(45) Date of Patent: Dec. 5, 2017

(54) METHOD AND SYSTEM FOR THREE-DIMENSIONAL IMAGING

(71) Applicant: Carestream Health, Inc., Rochester, NY (US)

(72) Inventors: Yannick Glinec, Shanghai (CN); Qinran Chen, Shanghai (CN)

(*) Notice: Subject to any disclaimer, the term of this patent is extended or adjusted under 35 U.S.C. 154(b) by 0 days.

(21) Appl. No.: 14/767,299

(22) PCT Filed: Mar. 11, 2013

(86) PCT No.: PCT/CN2013/072424
§ 371 (c)(1),
(2) Date: Aug. 12, 2015

(87) PCT Pub. No.: WO2014/139079
PCT Pub. Date: Sep. 18, 2014

(65) Prior Publication Data
US 2016/0014396 A1    Jan. 14, 2016

(51) Int. Cl.
*H04N 13/02*    (2006.01)
*G01B 11/24*    (2006.01)
(Continued)

(52) U.S. Cl.
CPC ....... *H04N 13/0296* (2013.01); *A61B 1/0005* (2013.01); *A61B 1/00055* (2013.01);
(Continued)

(58) Field of Classification Search
CPC .. G06K 9/22; G06K 2209/40; H04N 5/23238; H04N 13/2096; A61C 9/0053;
(Continued)

(56) References Cited

U.S. PATENT DOCUMENTS

| | | | |
|---|---|---|---|
| 2002/0006217 A1* | 1/2002 | Rubbert et al. | 382/131 |
| 2007/0171220 A1* | 7/2007 | Kriveshko | 345/419 |
| 2012/0062557 A1 | 3/2012 | Dillon et al. | 345/419 |

FOREIGN PATENT DOCUMENTS

| | | | | |
|---|---|---|---|---|
| CN | 101706263 A | | 5/2010 | ............. G01B 11/25 |
| EP | 2 428 162 A1 * | | 3/2012 | ............. A61B 5/107 |

(Continued)

OTHER PUBLICATIONS

International Search Report, dated Jul. 11, 2013 International Application No. PCT/CN2013/072424, 3 pages.

(Continued)

*Primary Examiner* — Andrew W Johns
(74) *Attorney, Agent, or Firm* — Thompson Hine LLP

(57) ABSTRACT

A method for three-dimensional imaging is provided, storing a first two-dimensional image of field of view of a scanning device at a first position where a first three-dimensional view of the object is captured with said handheld scanning device; estimating location metric of a second two-dimensional image of field of view of said scanning device at a second position relative to said first image while said scanning device is being moved from said first position to said second position; and generating instructions on providing feedback to the user based on said location metric; wherein said feedback is provided to indicate if said second position is adequate for capturing a second three-dimensional view. A system for three-dimensional imaging is provided as well.

19 Claims, 5 Drawing Sheets

(51) Int. Cl.
  *A61C 9/00* (2006.01)
  *A61C 19/05* (2006.01)
  *A61B 1/00* (2006.01)
  *A61B 1/24* (2006.01)
  *G06F 3/01* (2006.01)
  *G06K 9/22* (2006.01)
  *G06T 3/60* (2006.01)
  *G06T 11/60* (2006.01)
  *H04N 5/232* (2006.01)
  *G06T 7/30* (2017.01)

(52) U.S. Cl.
  CPC .............. *A61B 1/24* (2013.01); *A61C 9/0053* (2013.01); *A61C 19/05* (2013.01); *G01B 11/24* (2013.01); *G06F 3/016* (2013.01); *G06K 9/22* (2013.01); *G06T 3/60* (2013.01); *G06T 7/30* (2017.01); *G06T 11/60* (2013.01); *H04N 5/23238* (2013.01); *G06T 2200/04* (2013.01); *G06T 2200/24* (2013.01); *G06T 2207/10028* (2013.01); *G06T 2207/30036* (2013.01)

(58) Field of Classification Search
  CPC ............. G06T 2200/04; G06T 2200/24; G06T 2207/10028; G06T 2207/30036
  See application file for complete search history.

(56) References Cited

FOREIGN PATENT DOCUMENTS

| JP | 11-501174 A | 1/1999 | ............. H04N 1/107 |
| JP | 2002-027291 A | 1/2002 | ............. H04N 5/225 |
| JP | 2002-501349 A | 1/2002 | ............. H04N 13/02 |
| JP | 2005-050034 A | 2/2005 | ............. G06T 17/40 |
| JP | 2008-194108 A | 8/2008 | ............... A61B 1/24 |
| JP | 2011-524571 A | 1/2011 | ............. G06T 19/00 |
| JP | 2012-055695 A | 3/2012 | ............... A61B 1/24 |
| JP | 2012-066072 A | 4/2012 | ............... A61B 1/00 |

OTHER PUBLICATIONS

Supplementary Partial European Search Report, dated Oct. 27, 2016 for European Patent Application No. 13 877 840.2, 2 pages.

\* cited by examiner

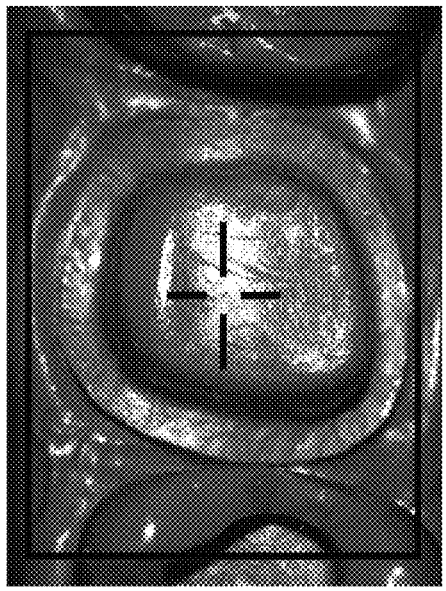
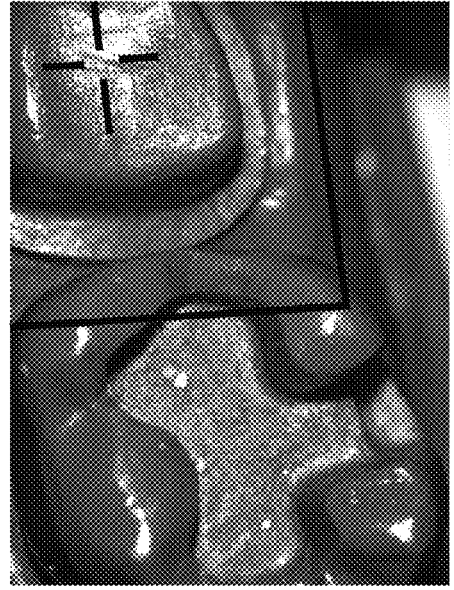
Fig.4a
Fig.4b
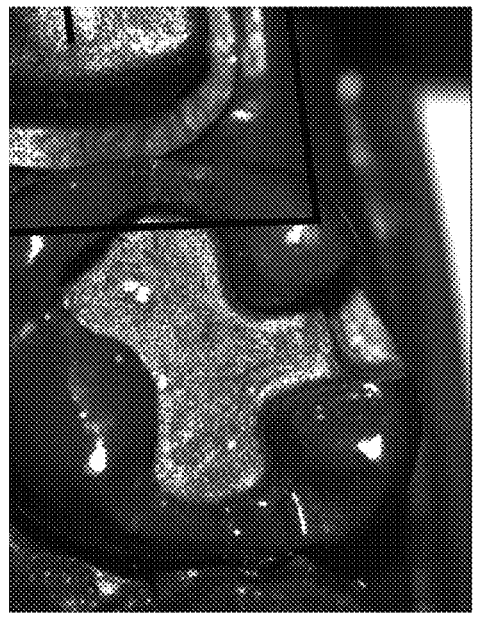
Fig. 4c

METHOD AND SYSTEM FOR THREE-DIMENSIONAL IMAGING

CROSS REFERENCE TO RELATED APPLICATIONS

This application claims the benefit of and is a U.S. National Phase filing of PCT Application PCT/CN2013/072424 filed Mar. 11, 2013 entitled "A METHOD AND SYSTEM FOR THREE-DIMENSIONAL IMAGING", in the name of Glinec et al.

TECHNICAL FIELD

This invention relates to three-dimensional (3D) imaging of physical object, and more particularly, it relates to a method and system for three-dimensional imaging with a handheld scanning device freely operated by a user.

BACKGROUND

Three-dimensional (3D) imaging technology has been playing an increasingly important role for a wide range of applications, including the production of movies and video games, computer-aided industrial design, orthotics and prosthetics, reverse engineering and prototyping, quality control and inspection, documentation of cultural artifacts, and the like. To facilitate the extensive use of three-dimensional imaging technique by ordinary people, electronic handheld 3D camera product configured with imaging optics have been developed. Due to its portability, such camera devices can be easily handled by the user to analyze a real-world object or environment as needed.

Generally speaking, 3D camera product is designed to collect data on the shape of the object and possibly its appearance, which is then recorded as data points within three-dimensional space. Once a point cloud of geometric samples on the surface of the subject has been obtained, these points can then be used to extrapolate the shape of the subject, for example be converted into a triangulated mesh and then a computer-aided design model. For most situations, it requires multiple scans from many different directions to produce a complete model of the object, usually at least one 3D view being obtained during one scan at a certain perspective. Multiple 3D views are then assembled into a full three-dimensional model, which is often referred to as a "stitching" process.

Various stitching algorithms have been developed, most of which require proper overlap between latest acquired view and previously acquired view to ensure successful and efficient stitching and thus enhance the quality of 3D modeling. For the handheld 3D camera or scanning device products which allow the user to operate freely, i.e. to collect three-dimensional views of the object from substantially random orientations or positions relative to the object, there may exist particular difficulties for the stitching process since a randomly captured view could only mislead the reconstruction, bringing extra burden on calculation rather than a desired result. Prior art does not provide guidance to the user between 3D view captures on how to appropriately locate the scanning device so that the 3D view to be captured may contain useful information for the stitching process. Rather, the operator shall use his or her own judgment on site, and it is often the case that with more scans being conducted, considerable computing time may be required, while the results might often be inaccurate.

BRIEF SUMMARY OF THE INVENTION

It is accordingly an object of the invention to provide a method and system for providing real-time feedback for three-dimensional imaging procedure during the free capture of individual 3D views with handheld scanning devices, which overcomes the above-mentioned disadvantages within the known devices of this general type and which enables more efficient and accurate 3D reconstructions.

With the foregoing and other objects in view, there provides a method for three-dimensional imaging, said method comprising: storing a first two-dimensional image of field of view of a scanning device at a first position where a first three-dimensional view of the object is captured with said handheld scanning device; estimating location metric of a second two-dimensional image of field of view of said scanning device at a second position relative to said first image while said scanning device is being moved from said first position to said second position; and generating instructions on providing feedback to the user based on said location metric; wherein said feedback is provided to indicate if said second position is adequate for capturing a second three-dimensional view.

On another aspect of the present invention, there is also provided a system for three-dimensional imaging, said system comprising: a handheld scanning device freely operated by a user to capture three-dimensional views of an object; a processing unit configured to: store a first two-dimensional image of field of view of said scanning device at a first position where a first three-dimensional view of the object is captured; estimate location metric of a second two-dimensional image of field of view of said scanning device at a second position relative to said first image while said scanning device is being moved from said first position to said second position; generate instructions on providing feedback to the user based on said location metric; and a feedback unit configured to provide said feedback to the user according to said instructions from said processing unit; wherein said feedback is provided to indicate if said second position is adequate for capturing a second three-dimensional view.

The present invention provides directly perceivable feedback on the location of the previously acquired 3D view relative to a new 3D view to be captured, so that the user may be fully aware if the place he or she locates the scanning device for the new 3D view is appropriate for 3D modeling. The feedback is based on the tracking of two-dimensional images in the viewfinder of the scanning device corresponding to the 3D views. Since the feedback is independent of any stitching algorithm in three-dimensional space, the present invention does not introduce noticeable processing cost and time increase. Rather, with the operator of the scanning device knowing where to conduct an effective scan, the 3D stitching process may be substantially enhances, in terms of both speed and quality.

Other features of the invention, its nature and various advantages will be apparent from the accompanying drawings and the following detailed description of certain preferred embodiments.

BRIEF DESCRIPTION OF THE DRAWINGS

The foregoing and other objects, features, and advantages of the invention will be apparent from the following more particular description of preferred embodiments as illustrated in the accompanying drawings, in which:

FIGS. 4a, 4b and 4c depict views for providing feedback to the user according to one embodiment of the present invention.

DETAILED DESCRIPTION

Figure 1:
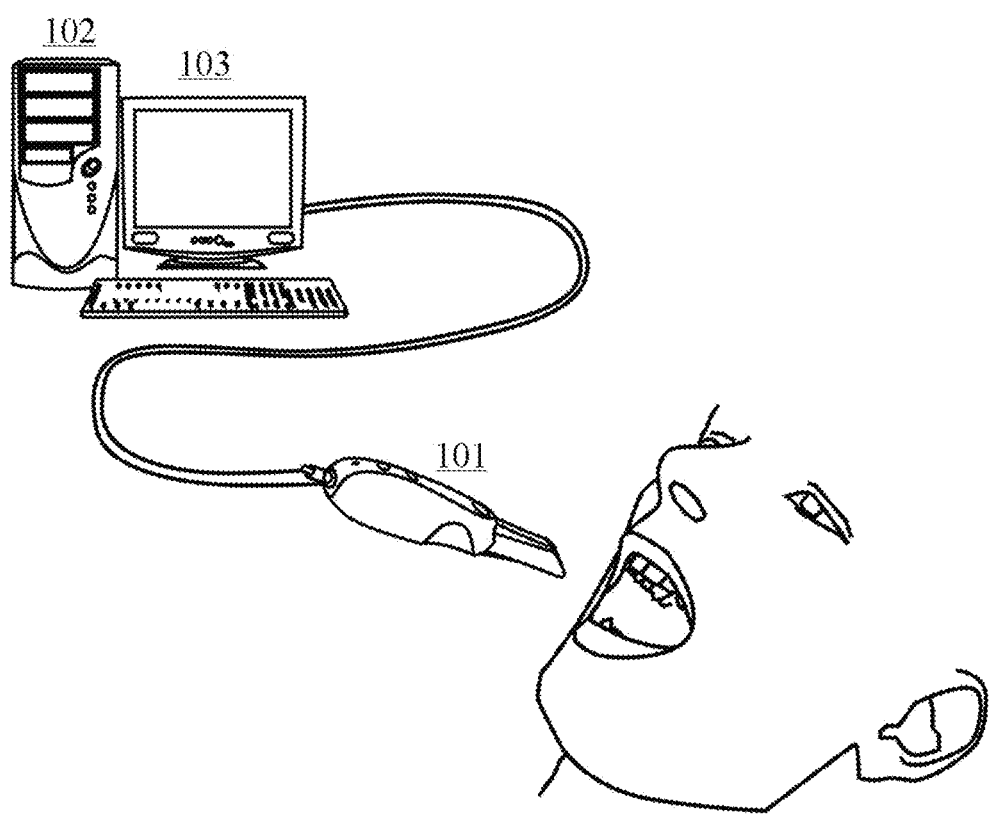
FIG. 1 illustrates a system for three-dimensional imaging according to one embodiment of the invention.

While the invention covers various modifications and alternative constructions, embodiments of the invention are shown in the drawings and will hereinafter be described in detail. However it should be understood that the specific description and drawings are not intended to limit the invention to the specific forms disclosed. On the contrary, it is intended that the scope of the claimed invention includes all modifications and alternative constructions thereof falling within the scope of the invention as expressed in the appended claims.

Unless defined in the context of the present description, otherwise, all technical and scientific terms used herein have the same meaning as commonly understood by one of ordinary skill in the art to which this invention belongs.

It is described below a technique for providing real-time feedback to a user operating a three dimensional scanning device for three-dimensional imaging. However, it will be appreciated that the inventive concepts disclosed herein are not limited to such applications, and may be usefully employed in a variety of imaging applications. For example, the system and method described herein may be usefully employed in two-dimensional imaging systems or other applications where the imaging could be enhanced by a real-time feedback. All such variations and alternative embodiments as would be apparent to one of ordinary skill in the art are intended to fall within the scope of this disclosure.

Moreover, by way of a non-limiting example, the methods and arrangements of the present disclosure may be illustrated by being used in dental implant imaging. However, it should be understood that the teaching of the present disclosure can be applied to similar 3D imaging procedure, where the generation of the object surface in three dimensions is based on stitching of several 3D views captured at arbitrary orientation relative to the object with a scanning device under free control of a user.

FIG. 1 illustrates a system for three-dimensional imaging according to one embodiment of the invention. System 100 may be applied to prosthodontics procedures designed to implant a dental prosthesis in the intra oral cavity, providing three-dimensional modeling result for a prosthesis such as a crown. According to the embodiment shown in FIG. 1, system 100 may at least comprise a handheld scanning device 101, a processing unit 102 and a feedback unit 103.

As shown in FIG. 1, the handheld scanning device is in the shape of a probe, which could be freely operated, i.e., positioned by a user. However, this kind of handheld scanning device, also termed as hand-piece herein for simplicity, could be configured into any shape, as long as it could provide the user with sufficient convenience in its moving and operating. Basically, the handheld scanning device 101 may be manipulated by the user to capture three-dimensional views of an object from different positions, for example, while there is generally no rules for the sequence of the 3D views to be captured. For example, hand-piece 101 may serve as an intra-oral camera in the illustrated embodiment, where the object could be the jaw, tooth or gum of a patient.

Figure 2:
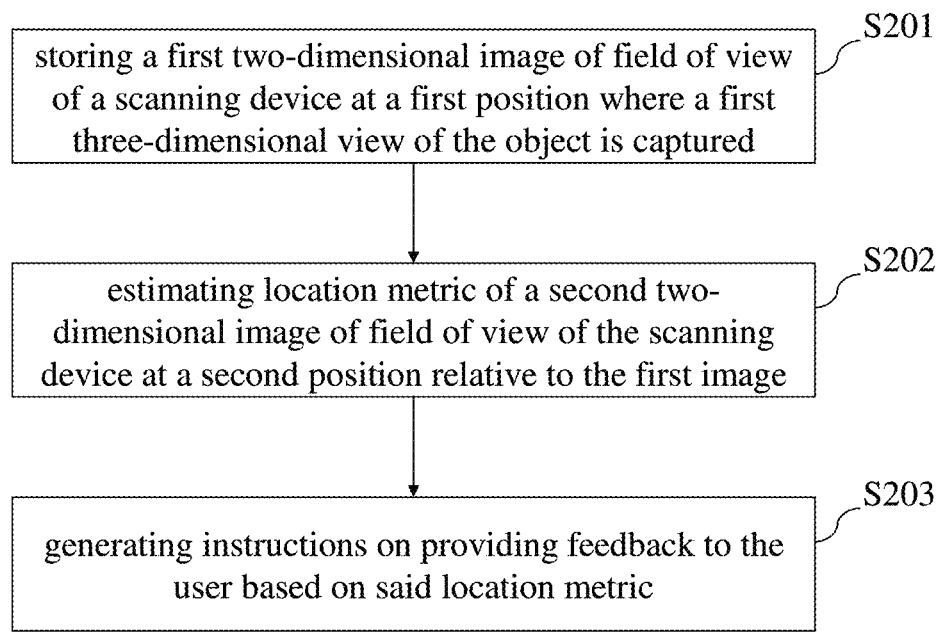
FIG. 2 illustrates a process for three-dimensional imaging according to one embodiment of the invention.

The processing unit 102 may be configured to execute the steps as illustrated in FIG. 2, where a process for three-dimensional imaging according to one embodiment of the present invention is illustrated. Particularly, the processing is configured to store (S201) a first two-dimensional image of field of view of scanning device 101 at a first position where a first three-dimensional view of the object is captured; estimate (S202) location metric of a second two-dimensional image of field of view of scanning device 101 at a second position relative to said first image while the scanning device 101 is being moved from said first position to said second position; and generate (S203) instructions on providing feedback to the user based on the location metric. In embodiments of the present invention, the feedback is provided to indicate if the second position is adequate for capturing a second three-dimensional view for stitching process in three-dimensional imaging procedure.

Processing unit 102 is shown as a personal computer in FIG. 1. It is to be understood that it may implemented in, for example, any suitable processing platform, computing platform, computing device, processing device, computing system, processing system, computer, processor, or the like, and may be implemented using any suitable combination of hardware and/or software, as may be suitable for specific applications or in accordance with specific design requirements.

As mentioned above, in order to obtain a view for the global surface of an object, more than one 3D views shall be successively captured from different perspectives and the three-dimensional data for each view may be "stitched" all together at the same time or stitched to existing three-dimensional model using various stitching algorithms. Either way, an appropriate overlap between the captured 3D views is critical to the success and efficiency of the stitching process and to the quality of the modeling result. While benefiting from the free control of the handheld equipment, users may not be fully aware of where to position the hand-piece so as to enhance the efficiency and accuracy of the 3D modeling procedure. For a 3D imaging system which is configured to provide visual image of field of view of the scanning device, the user often has no clue about the position where last 3D view was captured relative to the video image currently being shown on the screen after the movement of the scanning device.

Processing unit 102 is configured to generate instructions on providing feedback to the user between two 3D view captures, i.e., after one 3D view has been obtained and before another scan is to be conducted. With the help of such real-time feedback, users could be warned or notified if the current placement of the scanning device 101 is adequate for capturing another 3D view, which is advantageous to the stitching process.

As mentioned above, the instructions on providing feedback to the user is generated based on estimated location metric of a 2D image of field of view of scanning device 101 at its current position, i.e., the second image, relative to the stored image of its field of view at the previous position where last 3D view was captured, i.e., the first image. For example, the location metric may be estimated as the overlap between the first image and the second image or the rotation angle between the first image and the second image. In one embodiment of the present invention, if the overlap is estimated to be above 30% or if the rotation angle is estimated to be less than 30 degrees, feedback may be provided to indicate that the second position where a new 3D view is to be captured is acceptable for the stitching process.

For guarantee success of 3D imaging procedure, the goal is to estimate the overlap of a new 3D view with the mesh surface acquired during last scan. User guidance based on 3D reconstruction of the captured data during the movement of scanning device may provide more stable results, but also may suffer from real-time constraints and complexity of algorithm, which would probably bring no benefits. By contrast, in embodiments of the present invention, feedback on the placement of the scanning device is independent from the 3D reconstruction algorithm. The candidate position for a new 3D view is evaluated simply from a measure of relative location between corresponding two-dimensional images, assuming that the overlap between 3D views can be reflected by the overlap between corresponding 2D images. Perspective viewing, where object surfaces might be occluded, and missing parts in the 3D view (due to lack of signal in regions of low reflectivity for instance) are two reasons why this assumption is not valid. However, since the object of the present invention is only to guide the operator and provide reference information, the accuracy of this measure does not need to be extremely precise. The process for estimating location metric will be exemplified below with respect to FIG. 3.

Feedback unit 103 is designed to function according to the instructions from the processing unit 102, i.e., to provide said feedback to the user according to the instruction generated by processing unit 102.

In the embodiment as illustrated in FIG. 1, feedback unit 103 is implemented as a monitor, where live video images of field of view of scanning device 101 may be rendered to assist the operator in positioning the scanning device relative to the object. In one embodiments of the present invention. In this case, the instructions on providing feedback may include displaying representation of the first image superimposed on the live video images. This superposition of a sign of the first image may indicate to a user both where the scanning device 101 is currently positioned and how the scanning device has been moved relative to the position where last scan was conducted. To provide the effect of real-time tracking. The location and appearance of the representation may be configured to change with the moving of said scanning device, so that the user may have a clear vision of how the scanning device 101 has been moved from where last scan was conducted.

An example could be seen in FIG. 4a, FIG. 4b and FIG. 4c, where the representation of the first image is a rectangle with a cross inside. FIG. 4a shows the field of view of scanning device 101 at the first position when last 3D view was being captured, i.e., the first image, where the rectangle and the cross is located right in the middle of the screen without any distortion. FIG. 4b shows the field of view of scanning device 101 when it is positioned at a second site, where the deformation and displacement of the rectangle and the cross on the screen may reflect the rotation, translation and tilt of the scanning device relative to the position where last scan was conducted. The color code of the frame indicates a suitable position for acquisition of a 3D view. FIG. 4c shows the field of view of a scanning device 101 when positioned at another second site, where the orange color of the frame indicates a non-recommended place for acquisition of a 3D view. In some cases, the representation of the first frame may only be partially displayed, since the scanning device has been moved far away from the initial place.

Preferably, to provide a directly perceivable indication of whether the current position is appropriate to capture another 3D view, the representation of the first frame may be configured to present a first color, for example green to indicate the second position is adequate (FIG. 4b) and a second color, like orange to indicate the second position is not adequate (FIG. 4c).

In another embodiment of the present invention, feedback unit 103 may be implemented as a light emitting component integrated with scanning device 101, for example, attached to one side of the body of the scanning device. For example, the light emitting component may include any light projector and light emitting buttons or diodes. In one embodiment of the present invention, there may be a LED ring around the capture button on the hand-piece that can change the color of light. The light emitting component may emit light of a first color, for example green to indicate the second position is adequate and emit light of a second color, like red to indicate the second position is not adequate. In this case, whether or not any live vision of the captured image is provided, the user may be aware of how to locate the scanning device by looking at the emitted color directly from the hand-piece, without having to watch at the display of the processing unit.

In still another embodiment of the present invention, feedback unit 103 may be implemented as an image projector. Feedback as to the displacement of the scanning device 101 may be provided by projecting images onto the object through the image projector.

Figure 5:
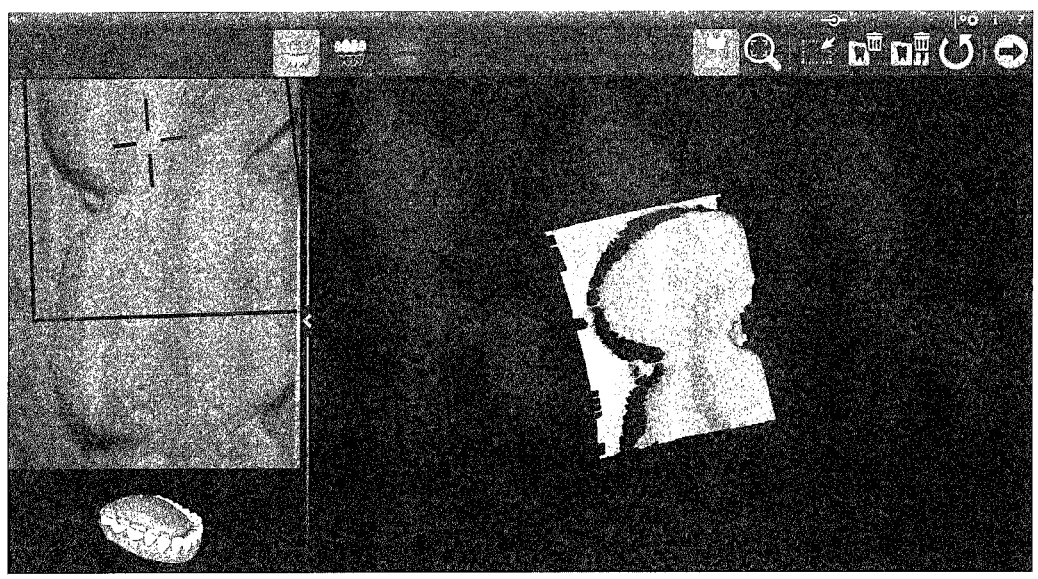
FIG. 5 depicts a view for providing feedback to the user according to another embodiment of the present invention.

FIG. 5 depicts an exemplary view for providing feedback through an image projector in dental application, where the object is the patient's teeth. The projected image could be the distorted rectangle and crosses as shown on the computer screen or could also be a projection of already acquired 3D views. The 3D surface on the right was acquired at the first position. Based on the estimated location metric of the second image relative to the first image, we have enough knowledge to place the 3D surface from the right onto the video frame, inside the rectangle, which may be shown as green. That is, the image projector may be configured to directly project the 3D surface on the right onto the teeth surface, at proper location relative to the current view. The live view is provided on the left for the purpose of illustration, while in practice, the user may see the 3D surface inside the mouth with his eyes, without looking at the screen.

With the help of appropriate feedback between two captures, computation resources could be saved to some degree since misleading or useless information resulted from the arbitrary positioning and orientation of the scanning device has been largely reduced. The stitching process for 3D imaging could be more smoothly and efficiently carried out, and thus enhancing accuracy of the final results.

It is to be understood by those skilled in the art that the structure of system 100 as illustrated in FIG. 1 is only provided for exemplary purpose. Though scanning device 101, processing unit 102 and feedback unit 103 are shown as separate pieces, they could be implemented as an integration. For example, processing unit 102 may be integrated within the hand-piece device, which may further equipped with a screen for providing real-time feedback. In another implementation, feedback unit 103 may also be incorporated into a processing device, like when a laptop is being used to communicate with the scanning device 101. Generally, embodiments of the present invention may include units and/or sub-units, which may be separate of each other or combined together, in whole or in part, and may be implemented using specific, multipurpose or general processors or controllers, or devices as are known in the art.

It is to be noted that stitching in two dimensions is much less complicated than the 3D stitching procedure. The two dimensional stitch could provide a transformation matrix, which contains the information on the spatial transform between corresponding pixel on the two images being stitched. Such transformation matrix is usually created as a square matrix, which provides a linear relationship between a 2D point from one image and a corresponding 2D points on a second image. In the field of this invention, a 2D point (x, y) is represented using homogeneous coordinates (x, y, 1). For homogeneous coordinates, such transformation matrix is defined as a homography matrix. In the field of computer vision, any two images of the same planar surface in space may be related by a homography matrix. A general 3×3 homography matrix H for transforming 2D pixel coordinates from $(x_2,y_2)$ to $(x_1,y_1)$ can be written as:

$$H = \begin{bmatrix} h_{11} & h_{12} & h_{13} \\ h_{21} & h_{22} & h_{23} \\ h_{31} & h_{32} & h_{33} \end{bmatrix}$$

such that:

$$\begin{bmatrix} wx_1 \\ wy_1 \\ w \end{bmatrix} = H \begin{bmatrix} x_2 \\ y_2 \\ 1 \end{bmatrix},$$

where w is a perspective parameter and is determined by that equation.

In the case of affine transform, $h_{31}=h_{32}=0$ and $h_{33}=1$. The remaining 6 degrees of freedom from the affine transform can be rewritten using an equivalent more classic representation as below:

$$H = \begin{bmatrix} s_x\cos\theta & s_x\sin\theta & t_x \\ -s_y\sin\theta + k\cos\theta & s_y\cos\theta + k\sin\theta & t_y \\ 0 & 0 & 1 \end{bmatrix}$$

wherein θ represents rotation angle between the two images, $(s_x, s_y)$ is a measure of scaling in two dimensions along the x and y axes of the second image respectively, w represents the skew between the two images, and $(t_x, t_y)$ is a measure of translation in two dimensions along x and y axes of the second image respectively In one embodiment of the present invention, stitching one image with another image to obtain the transformation matrix may include: 1. detect feature points in each image; 2. limit number of features; 3. extract feature descriptors for each image at feature locations; 4. match image descriptors using an exhaustive search algorithm, such as RANdom SAmple Consensus (RANSAC), which may be performed for the first image against the second image and vice versa; 5. keep symmetric matches only, i.e., when best match for feature f1 in the first image is f2 on the second image and best match for f2 is f1. One iteration of the RANSAC algorithm randomly picks 3 pairs of feature points from the above symmetric matches to compute a candidate transformation matrix, then determines how many other matches agree with the candidate transformation matrix by computing the distance between the transformed first point from the match and the target second point from the match. The match is said to agree with the transform if the distance falls below a predetermined threshold. Subsequent iterations of the RANSAC algorithm are performed, which may stop after a predetermined number of times. The candidate transformation matrix which had the highest number of matches that agree with it is selected as the transformation matrix.

This feature-based approach for image stitching is only described as an example. Any other strategies for computing transformation in computer vision may be used in embodiments of the present invention.

The estimation of the location metric between the first and second images can be done either directly between these images, or indirectly through the use of a reference image. At the beginning of the image sequence of field of views from scanning device 101 following the first frame, there should have enough overlap between first and second image for the stitching to be successful. But as the hand-piece moves away, the overlap between these two frames might not be sufficient to obtain accurate location metric. This explains why it is desired to have a reference image, which is selected during the image sequence of field of views, acting as an intermediate to allow location metric of the second image relative to the first image to be determined even when the first and second images don't overlap anymore.

Figure 3:
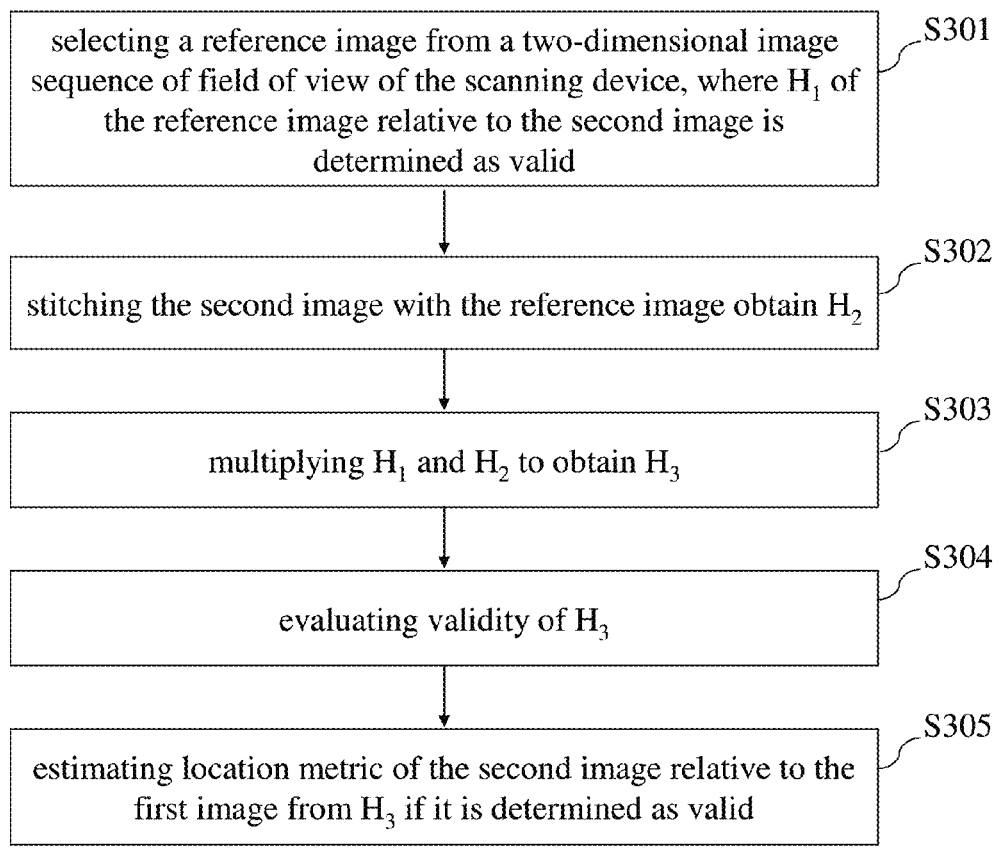
FIG. 3 illustrates a process for estimating location metric of one two-dimensional image of field of view of the scanning device relative to another.

FIG. 3 illustrates a process for estimating location metric of one two-dimensional image of field of view of the scanning device relative to another. As discussed above, the feedback to indicate if the second position is preferable for capturing a new 3D view is based on the estimated location metric of the second image relative to the first image. As illustrated in FIG. 3, to estimate said location metric, the processing unit 102 may be configured to first select a reference image from a two-dimensional image sequence of field of view of scanning device 101 at step 301, where the transformation matrix $H_1$ from that reference image to the first frame was determined to be valid. For instance, reference images can be taken at a specific time interval, such as every 500 ms.

At step 302, the second image is stitched onto the reference image to obtain a transformation matrix $H_2$.

At step 303, $H_2$ is then multiplied with $H_1$ to obtain a third transformation matrix $H_3$, which is assumed to represent the transformation between the first image and the second image.

Without loss of generalization, the reference image could be equal to the first image, in which case $H_1$ equals the identity matrix and doesn't need to be evaluated numerically. This is equivalent to the direct evaluation of the transformation between the first and second frame as described above.

There may exist situations where the computation of the transformation matrix between two images might not be possible. For instance, the number of features or the number of feature matches might not be enough to determine any transformation. In such case, the stitching fails, otherwise the stitching succeeds.

At step 304, in case the stitching succeeds, the obtained transformation matrix $H_3$ must be evaluated to check if it is valid and determine a measure of the spatial relationship between the first image and the second image. In one embodiment of the present invention where $H_1$, $H_2$ and $H_3$ is affine transformation matrix, the validity of transformation matrix $H_3$ may include decomposing $H_3$ to obtain at least one parameter describing spatial correspondence between pixels in the second image and the first image, that is to extract parameters such as θ, w, ($s_x$, $s_y$), ($t_x$, $t_y$). The extracted parameters may be compared to predetermined thresholds so as to determine if $H_3$ is valid. For example, if the scale value of ($s_x$, $s_y$) for x and y axes both lie in the range of [0.5, 2], then $H_3$ could be considered as acceptable. The same ideas applies to the other parameters.

In another embodiment of the present invention, evaluating the validity of transformation matrix $H_3$ may include: applying $H_3$ to the second image to obtain an intermediate image, that is to multiply $H_3$ with the pixel matrix of the second image and then calculating similarity between the intermediate image and the first image. A measure of similarity may be obtained by calculating normalized cross correlation (NCC) or normalized mutual information between the intermediate image and the first image, the former may lie in the range of [−1, 1] and the latter in the range of [0, 1]. The similarity could be compared with a predetermined threshold to determine if $H_3$ is valid.

At step 305, if $H_3$ is determined as valid, the location metric of the second image relative to the first image is estimated from this matrix. As mentioned above, the location metric for example could be a measure of overlap or rotation angle between the two images. Decomposition results of a valid $H_3$ between the second and first image could provide a solid estimation of location metric, such as the rotation angle. Decomposition of the transformation matrix into a 3×3 rotation matrix and a 3×1 translation vector may require the knowledge of intrinsic camera parameters, which can be obtained through camera calibration procedures in the field of computer vision. The rotation angle of a rotation θ matrix can be computed using the following relationship in a rotation matrix R: trace(R)=1+2 cos(θ). The fraction of pixels in the intermediate image which contains information from the second image could provide the estimation of overlap between the two images.

In practice, the processing unit is configured to store several reference images during the movement of the scanning device, where the reference frame could be sampled at a certain interval. In order to limit the amount of data stored, the total number of reference images may be limited, therefore some references may be replaced by new ones after a while. The use of multiple reference images allows the tracking to continue/recover faster by switching to another reference image if tracking doesn't succeed any longer with the current frame. The tracking is said to have a limited history. When a reference image gets stored, the corresponding transformation matrix $H_1$ is also stored along with the reference image. This way $H_1$ never needs to be recomputed. The same selected reference frame might be reused for subsequent second image in the captured image sequence.

The transformation matrix between images is denoted with a single matrix, regardless of the mapping direction, but to be precise, if transformation matrix H corresponds to the mapping from second image pixel coordinate onto first image pixel coordinate, the opposite relationship from first image pixel coordinate to second image pixel coordinate is obtained using the inverse of the transformation matrix H.

Although embodiments of the invention are not limited in this regard, the terms "plurality" and "a plurality" as used herein may include, for example, "multiple" or "two or more". The terms "plurality" or "a plurality" may be used throughout the specification to describe two or more components, devices, elements, units, parameters, or the like.

It should be noted that the aforesaid embodiments are illustrative of this invention instead of restricting it, substitute embodiments may be designed by those skilled in the art without departing from the scope of the claims below. The wordings such as "include", "including", "comprise" and "comprising" do not exclude elements or steps which are present but not listed in the description and the claims. It also shall be noted that as used herein and in the appended claims, the singular forms "a", "an", and "the" include plural referents unless the context clearly dictates otherwise. This invention can be achieved by means of hardware including several different elements or by means of a suitably programmed computer. In the unit claims that list several means, several ones among these means can be specifically embodied in the same hardware item. The use of such words as first, second, third does not represent any order, which can be simply explained as names.

The invention claimed is:

1. A method for three-dimensional imaging, said method comprising:
   storing a first two-dimensional image of field of view of a scanning device at a first position where a first three-dimensional view of an object is captured with said scanning device freely operated by a user;
   estimating location metric of a second two-dimensional image of field of view of the scanning device at a second position relative to said first image while said scanning device is being moved from said first position to said second position;
   generating instructions on providing feedback to the user based on said location metric; wherein
   said feedback is provided to indicate if said second position is adequate for capturing a second three-dimensional view, wherein providing feedback includes providing user perceivable light of a first color to indicate said second position is adequate and providing user perceivable light of a second color to indicate said second position is not adequate.

2. The method according to claim 1, wherein said location metric is estimated as one of the following: overlap between said first image and said second image; and rotation angle between said first image and said second image.

3. The method according to claim 2, wherein if said overlap is above 30% or if said rotation angle is less than 30 degrees, providing feedback indicating that said second position is adequate for capturing said second three-dimensional view.

4. The method according to claim 1, wherein providing feedback includes displaying representation of said first image superimposed on live video images of field of view of said scanning device on a screen, and wherein
   the location and appearance of said representation on the screen is configured to change with the motion of said scanning device; and wherein
   said representation is configured to present the first color to indicate said second position is adequate and the second color to indicate said second position is not adequate.

5. The method according to claim 4, wherein said representation of said first image is configured as a rectangle with a cross inside.

6. The method according to claim 1, wherein providing feedback includes emitting light of the first color to the object to indicate said second position is adequate and emitting light of the second color to indicate said second position is not adequate.

7. The method according to claim 1, wherein providing feedback includes projecting images onto the object.

8. The method according to claim 1, wherein estimating location metric of said second image relative to said first image including:

a) selecting a reference image from a two-dimensional image sequence captured during its displacement from said first position to said second position, where transformation matrix $H_1$ of said reference image relative to the first image has been determined as valid;
b) stitching said second image with the reference image to obtain transformation matrix $H_2$;
c) multiplying $H_1$ and $H_2$ to obtain transformation matrix $H_3$;
d) evaluating the validity of transformation matrix $H_3$;
e) estimating said location metric of said second image relative to said first image from transformation matrix $H_3$ if it is determined as valid.

9. The method according to claim 8, wherein transformation matrix $H_1$, $H_2$ and $H_3$ is affine transformation matrix.

10. The method according to claim 9, wherein evaluating the validity of said affine transformation matrix $H_3$ includes
decomposing $H_3$ to obtain at least one parameter describing spatial correspondence between pixels in said second image and said first image; and
comparing the at least one parameter with predetermined thresholds to determine if said affine transformation matrix $H_3$ is valid, wherein
the at least one parameter is selected from the group of scale for both x and y axes, rotation angle, skew and translation for both x and y axes between said second image and said first image.

11. The method according to claim 9, wherein
stitching one image with another image to obtain transformation matrix includes matching at least three pairs of feature points between the two images.

12. The method according to claim 8, wherein evaluating the validity of transformation matrix $H_3$ includes
applying transformation matrix $H_3$ to said second image to obtain an intermediate image;
calculating similarity between said intermediate image and said first image; and
comparing the similarity with a predetermined threshold to determine if transformation matrix $H_3$ is valid.

13. The method according to claim 1, wherein the scanning device is an intra-oral camera.

14. The method according to claim 1, wherein the object is the jaw, tooth or gum of a patient, an implant or a preparation.

15. A system for three-dimensional imaging, said system comprising:
a dental 3D scanner freely operated by a user to capture three-dimensional views of an object;
a processor configured to:
store a first two-dimensional image of field of view of said scanner at a first position where a first three-dimensional view of the object is captured;
estimate location metric of a second two-dimensional image of field of view of said scanner at a second position relative to said first image while said scanner is being moved from said first position to said second position;
generate instructions on providing feedback to the user based on said location metric; and
a user perceivable feedback unit configured to provide said feedback according to said instructions from said processor; wherein
said feedback is provided to indicate if said second position is adequate for capturing a second three-dimensional view, where estimating location metric of said second image relative to said first image including:

a) selecting a reference image from a two-dimensional image sequence captured during its displacement from said first position to said second position, where transformation matrix $H_1$ of said reference image relative to the first image has been determined as valid;
b) stitching said second image with the reference image to obtain transformation matrix $H_2$;
c) multiplying $H_1$ and $H_2$ to obtain transformation matrix $H_3$;
d) evaluating the validity of transformation matrix $H_3$;
e) estimating said location metric of said second image relative to said first image from transformation matrix $H_3$ if it is determined as valid.

16. The system according to claim 15, wherein said location metric is estimated as one of the following: overlap between said first image and said second image; and rotation angle between said first image and said second image, wherein if said overlap is above 30% or if said rotation angle is less than 30 degrees, providing feedback indicating that said second position is preferable for capturing said second three-dimensional view.

17. The system according to claim 15, wherein said feedback unit comprising a monitor for displaying live video images of field of view of said scanner;
said instructions on providing feedback including displaying representation of said first image superimposed on said live video images; and wherein
the location and appearance of said representation is configured to change with the motion of said scanner; and wherein
said representation is configured to present a first color to indicate said second position is adequate and a second color to indicate said second position is not adequate.

18. A method for three-dimensional imaging, said method comprising:
storing a first two-dimensional image of field of view of a scanning device at a first position where a first three-dimensional view of an object is captured with said scanning device freely operated by a user;
estimating location metric of a second two-dimensional image of field of view of the scanning device at a second position relative to said first image while said scanning device is being moved from said first position to said second position;
generating instructions on providing feedback to the user based on said location metric; wherein
said feedback is provided to indicate if said second position is adequate for capturing a second three-dimensional view, where said location metric is estimated as one of the following: overlap between said first image and said second image; and rotation angle between said first image and said second image, and where when said overlap is above 30% or when said rotation angle is less than 30 degrees, providing feedback indicating that said second position is adequate for capturing said second three-dimensional view.

19. An apparatus for three-dimensional imaging, comprising:
means for storing a first two-dimensional image of field of view of a scanning device at a first position where a first three-dimensional view of an object is captured with said handheld scanning device freely operated by a user;
means for estimating location metric of a second two-dimensional image of field of view of a scanning device at a second position relative to said first image while said scanning device is being moved from said first position to said second position;

means for providing perceivable feedback to the user based on said location metric; wherein said perceivable feedback is provided to indicate if said second position is adequate for capturing a second three-dimensional view, where said location metric is estimated at least as one of the following: overlap between said first image and said second image; and rotation angle between said first image and said second image, and where when said overlap is above 30% or when said rotation angle is less than 30 degrees, providing feedback indicating that said second position is adequate for capturing said second three-dimensional view.

* * * * *